US009671325B2

(12) United States Patent
Takeda et al.

(10) Patent No.: US 9,671,325 B2
(45) Date of Patent: Jun. 6, 2017

(54) PARTICLE MEASURING DEVICE

(71) Applicant: Fuji Electric Co., Ltd., Kanagawa (JP)

(72) Inventors: Naoki Takeda, Kanagawa (JP); Kazuhiro Koizumi, Kanagawa (JP); Takamasa Asano, Tokyo (JP); Yoshiki Hasegawa, Tokyo (JP)

(73) Assignee: FUJI ELECTRIC CO., LTD., Kanagawa (JP)

(*) Notice: Subject to any disclaimer, the term of this patent is extended or adjusted under 35 U.S.C. 154(b) by 0 days.

(21) Appl. No.: 15/068,302

(22) Filed: Mar. 11, 2016

(65) Prior Publication Data

US 2017/0003221 A1 Jan. 5, 2017

(30) Foreign Application Priority Data

Jul. 2, 2015 (JP) ................................ 2015-133395

(51) Int. Cl.
*G01N 21/00* (2006.01)
*G01N 15/14* (2006.01)
*G01N 15/02* (2006.01)

(52) U.S. Cl.
CPC ..... *G01N 15/1434* (2013.01); *G01N 15/0205* (2013.01); *G01N 15/1456* (2013.01); *G01N 2015/1486* (2013.01)

(58) Field of Classification Search
CPC .............. G01N 21/53; G01N 15/1459; G01N 15/0211; G01N 15/1404; G01N 2021/052; G01N 2015/1493; G01N 2015/1087
USPC ................................................ 356/335–343
See application file for complete search history.

(56) References Cited

U.S. PATENT DOCUMENTS 4,685,802 A 8/1987 Saito et al.
5,033,851 A * 7/1991 Sommer ........... G01N 15/0205 356/338
5,642,193 A * 6/1997 Girvin ............... G01N 15/1404 250/222.2
5,726,753 A * 3/1998 Sandberg .............. G01N 15/02 356/337
5,751,422 A * 5/1998 Mitchell ............... G01N 21/53 356/337
5,793,485 A * 8/1998 Gourley ............ G01N 15/1429 356/318

(Continued)

FOREIGN PATENT DOCUMENTS

JP S59-104533 A 6/1984
JP H6-21860 B2 3/1994
JP 2005-172465 A 6/2005

*Primary Examiner* — Hoa Pham
(74) *Attorney, Agent, or Firm* — Chen Yoshimura LLP

(57) ABSTRACT

A particle measuring device includes: an optical resonator that reflects laser light back and forth between two facing reflective mirrors in order to amplify an energy of that laser light and form resonant laser light; a particle transport unit that transports particles in an aerosol to be measured across a beam path of the resonant laser light; a scattered light receiving unit that receives scattered light produced when the particles in the aerosol are irradiated by the resonant laser light; and a processor that receives light reception signals from the scattered light receiving unit, wherein the processor outputs light reception pulses according to the light reception signals and calculates time intervals between the light reception pulses that are temporally adjacent.

11 Claims, 4 Drawing Sheets

(56) References Cited

U.S. PATENT DOCUMENTS

| | | | | |
|---|---|---|---|---|
| 7,440,100 B2* | 10/2008 | Siemens | ................ | G01N 21/53 |
| | | | | 356/335 |
| 2003/0223062 A1* | 12/2003 | Matsuda | ............ | G01N 15/1456 |
| | | | | 356/338 |
| 2003/0235230 A1* | 12/2003 | Thornton | ................ | H01S 5/183 |
| | | | | 372/97 |
| 2004/0080747 A1* | 4/2004 | Cerni | ..................... | G01N 15/14 |
| | | | | 356/338 |
| 2011/0303859 A1* | 12/2011 | Lofstrom | ........... | G01N 15/1427 |
| | | | | 250/573 |
| 2013/0269424 A1* | 10/2013 | Jarrell | ................ | G01N 15/1429 |
| | | | | 73/61.48 |

* cited by examiner

TEM00

TEM01

TEM02

PARTICLE MEASURING DEVICE

BACKGROUND OF THE INVENTION

Technical Field

The present invention relates to a particle measuring device suitable for measuring particles suspended in a gas such as air (that is, an aerosol).

Background Art

Particle measuring devices in which particles suspended in a gas such as air (that is, an aerosol) are formed into a beam shape and then the resulting flow path is irradiated with laser light to measure the particles are one type of conventional, well-known particle measuring devices used for purposes such as monitoring semiconductor manufacturing environments or measuring particulate contaminates in the atmosphere. In this type of device, the scattered light produced when the laser light hits the particles is detected and used to evaluate the particles, and therefore the intensity of the laser light used to irradiate the particles is one of key factors in achieving high sensitivity. However, due to the principles behind generation of laser light, the intensity of the laser light produced by the laser emitter inevitably decreases to some degree when that light is extracted.

In order to solve this problem, Patent Document 1, for example, discloses a scattered light-type particle detector in which a particle flow path is formed within an external mirror-type laser resonator, and the particles are measured by irradiating them with laser light which has experienced no loss in energy. Moreover, Patent Document 2, for example, discloses a particle detection device in which an optical resonator is provided separately from the laser resonator and used to amplify the energy of the laser light in order to create resonant laser light. A particle flow path is formed within the optical resonator, and the particles are measured by irradiating them with the resonant laser light. Furthermore, Patent Document 3, for example, discloses a particle measuring device that includes an external optical resonator for the same purpose as in Patent Document 2, and the external optical resonator includes a detector that monitors the wavelength of the amplified-energy resonant laser light. The particle measuring device disclosed in Patent Document 3 also includes a mechanism that adjusts the distance between reflective mirrors in the external optical resonator according to the difference between the detected resonant wavelength and the wavelength of the laser emitter.

RELATED ART DOCUMENTS

Patent Documents

Patent Document 1: Japanese Patent Application Laid-Open Publication No. S59-104533
Patent Document 2: Japanese Examined Patent Application Publication No. H6-21860
Patent Document 3: Japanese Patent Application Laid-Open Publication No. 2005-172465

SUMMARY OF THE INVENTION

Typical laser resonant modes include modes such as TEM00, TEM01, and TEM02, and the intensity distributions observed in a cross section of a laser are different for each resonant mode. Conventional particle measuring devices that include particle measuring features, such as a particle counter, measure the number of particles by counting pulses of scattered light produced when the particles move across the laser beam. However, if the resonant mode changes during measurement due to vibrations or the like, the number of pulses of scattered light counted may no longer correspond to the number of particles. Moreover, when the resonant mode changes, the light intensity also changes. This can make it impossible to measure particle size or the like normally according to the relationship between the intensity of the resonant laser light and the intensity of the pulses of scattered light.

It is also possible to use a camera (an array sensor) or the like that is sensitive to the resonant wavelength and can directly measure the resonant mode of the optical resonator in order to monitor the laser resonant mode. However, doing this not only requires using complicated signal processing techniques such as image processing but also obviously requires the camera itself, which increases the overall cost of the particle measuring device.

The present invention was made in view of the above-mentioned problems and aims to provide a particle measuring device in which the resonant mode of the resonant laser light used to measure the particles as well as changes in the resonant mode can be detected using a device that has a simple configuration. Accordingly, the present invention is directed to a scheme that substantially obviates one or more of the problems due to limitations and disadvantages of the related art.

Additional or separate features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and other advantages and in accordance with the purpose of the present invention, as embodied and broadly described, in one aspect, the present disclosure provides a particle measuring device for measuring particles in an aerosol, including: an optical resonator that causes laser light to travel back and forth between two opposing reflective mirrors in order to amplify an energy of the laser light and form resonant laser light; a particle transport unit configured to transport the particles in the aerosol across a beam path of the resonant laser light so as to generate a stream of the particles crossing the beam path; a scattered light receiving unit configured to receive scattered light that is produced when the particles in the aerosol are irradiated by the resonant laser light, and output a light reception signal in accordance with the received scattered light for each scattering event; and a processor that receives the light reception signal from the scattered light receiving unit for each event of the reception of the scattered light, wherein the processor outputs a light reception pulse in accordance with each light reception signal from the scattered light receiving unit, and derives time intervals between light reception pulses that are temporally adjacent.

The present particle measuring device makes it possible to achieve high-sensitivity measurements of particles suspended in an aerosol to be measured by irradiating those particles with resonant laser light (that is, laser light in which the energy has been amplified). The present particle measuring device also makes it possible to detect the resonant mode of the resonant laser light as well as changes in the resonant mode by outputting light reception pulses corresponding to the scattered light produced when the resonant laser light hits the particles and then calculating the time intervals between temporally adjacent light reception pulses.

In the present invention, it is preferable that the processor further derive a frequency distribution of the derived time intervals. This makes it possible to detect the resonant mode of the resonant laser light as well as changes in the resonant mode with higher sensitivity and better precision.

Furthermore, it is preferable that the processor determine a resonant mode of the resonant laser light based on one or more of the derived time intervals between the adjacent pulses or a frequency distribution of the derived time intervals. This makes it possible to determine whether the resonant mode of the resonant laser light used to measure the particles is normal as well as monitor for changes in the resonant mode, thereby making it possible to maintain the precision of the particle measuring device.

Moreover, it is preferable that the optical resonator include a reflective mirror adjustment unit that adjusts the reflective mirrors in accordance with the determination of the resonant mode by the processor. This makes it possible to adjust the angle or the like of the reflective mirrors of the optical resonator when the resonant mode of the resonant laser light changes, thereby making it possible to return the resonant mode of the resonant laser light back to normal.

Furthermore, it is preferable that the particles in the aerosol cross the beam path of the resonant laser light formed by the optical resonator inside the optical resonator. This makes it possible to directly irradiate the particles in the aerosol to be measured with the resonant laser light formed in the optical resonator, thereby making it possible to measure the particles with high sensitivity.

Moreover, it is preferable that, in the optical resonator, a laser emitter be provided on a surface of one of the reflective mirrors on a side thereof opposite to where the resonant laser light is formed, and the optical resonator be configured such that laser light produced by introducing a prescribed excitation source to the laser emitter enters the optical resonator through the one of the reflective mirrors and goes on to become the resonant laser light. This makes it possible to make the particle measuring device more compact.

The present particle measuring device makes it possible to achieve high-sensitivity measurements of particles suspended in an aerosol to be measured by irradiating those particles with resonant laser light (that is, laser light in which the energy has been amplified). The present particle measuring device also makes it possible to detect the resonant mode of the resonant laser light as well as changes in the resonant mode by outputting light reception pulses corresponding to the scattered light produced when the resonant laser light hits the particles and then calculating the time intervals between temporally adjacent light reception pulses. This, in turn, makes it possible to guarantee the precision of the particle measuring device using a simpler configuration than a configuration that includes a dedicated detector.

It is to be understood that both the foregoing general description and the following detailed description are exemplary and explanatory, and are intended to provide further explanation of the invention as claimed.

DETAILED DESCRIPTION OF EMBODIMENTS

Next, the present invention will be described in detail with reference to figures.

Figure 1:
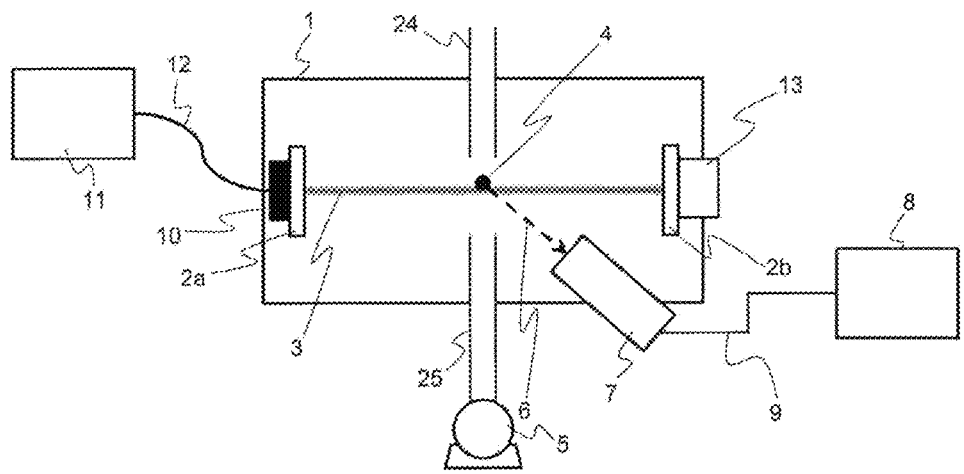
FIG. 1 is a plan view schematically illustrating a particle measuring device according to Embodiment 1 of the present invention.

FIG. 1 schematically illustrates the configuration of a particle measuring device 100 according to Embodiment 1 of the present invention. The particle measuring device 100 includes an optical resonator 1. The optical resonator 1 includes a pair of facing reflective mirrors 2a and 2b. Laser light travels back and forth between the reflective mirrors 2a and 2b, thereby amplifying the energy of the laser light and producing resonant laser light 3. Next, the basic structure of the optical resonator 1 will be described in more detail. One of the reflective mirrors 2a is partially transmissive and has a portion that transmits laser light. The other reflective mirror 2b is highly reflective and completely or substantially completely reflects the laser light. Furthermore, in the initial state when the laser light passes through the partially transmissive reflective mirror 2a and enters the optical resonator 1, the laser light travels back and forth across the prescribed distance between the reflective mirrors 2a and 2b, thereby producing a standing wave. The effects of interference reduce the energy of wavelengths other than a prescribed wavelength until only energy of that prescribed wavelength is stored. This results in the formation of the resonant laser light 3.

The particle measuring device 100 also includes a particle transport unit (reference characters 24 and 25 in FIG. 1) that transports particles 4 suspended in an aerosol to be measured. The particle transport unit concentrates the incoming aerosol into a beam shape that flows across the beam path of the resonant laser light 3 such that all or substantially all of the particles 4 get irradiated by the resonant laser light 3. Specific examples of the particle transport unit include configurations such as the sheath air nozzle in the particle measuring device described in Japanese Patent Application Laid-Open Publication No. 2012-189483, for example. The particle transport unit may also be an aerodynamic lens or the like that includes a constricting mechanism formed inside a tube-shaped member such that when a sample gas is passed through the tube-shaped member, the particles suspended in the sample gas are output in a beam shape. The particle transport unit may also be an optically transparent capillary tube or the like such as a fused quartz tube approximately 0.1 to 1 mm in inner diameter and approximately 10 mm in length that satisfies conditions that produce a particle beam of a prescribed diameter when the sample is passed therethrough.

In the embodiment illustrated in FIG. 1, a sheath air nozzle is used as the particle transport unit. This sheath air nozzle includes a sample discharge nozzle 24 that discharges the sample that includes the particles 4 in a direction orthogonal to the resonant laser light 3 and a sample recovery nozzle 25 that is arranged facing the sample discharge nozzle 24 and recovers the sample that includes the particles 4. Furthermore, a suctioning pump 5 draws the particles 4 suspended in the aerosol dispersion medium from the sample discharge nozzle 24 side to the sample recovery nozzle 25 side.

Figure 2:
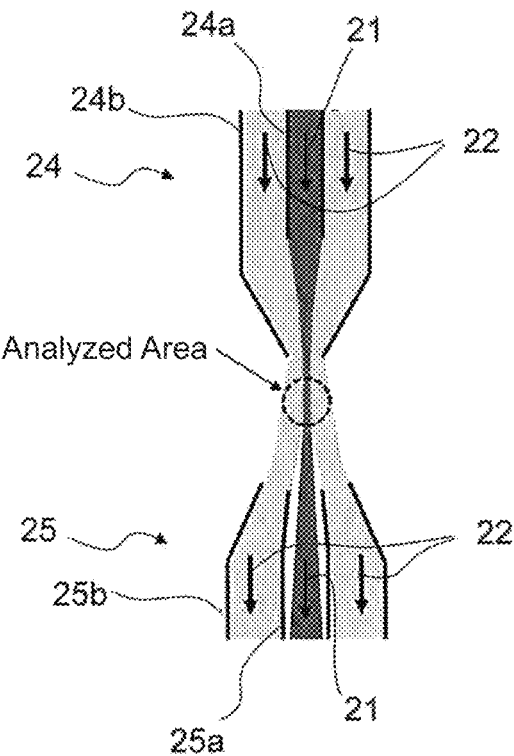
FIG. 2 is a cross-sectional view schematically illustrating a sheath air nozzle.

Next, the characteristics of the sheath air nozzle will be described in more detail with reference to FIG. 2. As illustrated in FIG. 2, the sample discharge nozzle 24 of the sheath air nozzle 20 has a two-layer structure that includes an internal nozzle 24a and an external nozzle 25b that is arranged around the outside of the internal nozzle 24a and has a greater outer diameter than the internal nozzle 24a. One end of the internal nozzle 24a (the upper end in FIG. 2) is connected to a duct (not illustrated in the figure) that brings in the sample 21, and one end of the external nozzle 24b (the upper end in FIG. 2) is connected to a duct (not illustrated in the figure) that brings in sheath air 22. Furthermore, the sample 21 flows through the internal nozzle 24a due to the pressure difference or the like between the inside and outside of a vessel to which the sample discharge nozzle 24 is attached. Using a flow rate adjustment unit (not illustrated in the figure), the flow rate of the sheath air 22 through the region around the internal nozzle 24a (that is, through the ring-shaped region between the internal nozzle 24a and the external nozzle 24b) is adjusted to be 5 to 10 times the flow rate of the sample 21. Moreover, the other end of the external nozzle 25b (the lower end in FIG. 2) has a tapered shape. Due to this structure, the sample 21 is enveloped by the clean sheath air 22 and discharged from the sample discharge nozzle 24 as an extremely fine stream. As this fine stream passes through an analysis region, the particles contained in the sample 21 are transported through the analysis region in a beam shape.

As illustrated in FIG. 2, the sample recovery nozzle 25 of the sheath air nozzle 20 has substantially the same two-layer structure as the sample discharge nozzle 24 and includes an internal nozzle 25a and an external nozzle 25b. The ends of the internal nozzle 25a and the external nozzle 25b (the upper ends in FIG. 2) both have a tapered shape. Furthermore, the cross-sectional shape of this end of the internal nozzle 25a is formed to be the same as the cross-sectional shape of the flow path of the sample 21 immediately prior to being sucked in by the sample recovery nozzle 25. Due to this, the sample 21 discharged from the sample discharge nozzle 24 is sucked into the internal nozzle 25a, and the sheath air 22 discharged from the sample discharge nozzle 24 is sucked into the region around the internal nozzle 25a (that is, into the ring-shaped region between the internal nozzle 25a and the external nozzle 25b). Moreover, the shape of the sample recovery nozzle 25 (that is, the inner diameters of the nozzles 25a and 25b, and the like) is configured such that the flow velocities of the sample 21 and the sheath air 22 do not change significantly before or after being sucked into the sample recovery nozzle 25. This structure maintains the flow rate ratio of 5 to 10 times between the sheath air 22 and the sample 21, thereby preventing decreases in the particle concentration and making it possible to smoothly transport the sample 21 to the next analysis region as necessary.

The particle measuring device 100 also includes a scattered light receiving unit 7 that receives scattered light 6 produced when the aerosol particles 4 are irradiated by the resonant laser light 3. Any unit may be used for the scattered light receiving unit as long as the selected unit can receive the scattered light produced each time one of the particles crosses the resonant laser light 3. Examples of a scattered light receiving unit include devices such as a scattered light detection device that includes a detection element such as a photomultiplier tube or a photodiode that is optically coupled to a light-receiving optical system as well as a driver circuit for the detection element. Moreover, the scattered light-type particle counting device disclosed in Japanese Patent Application Laid-Open Publication No. S61-14543 includes a light-collecting optical system that collects the scattered light from the particles at a plurality of positions and photodetectors that convert the light collected by the light-collecting optical system to electrical signals, thereby making it possible to calculate the number and size (or size distribution) of the particles according to the strength of the scattered light at each position. A device such as this, in which scattered light from a single particle can be received at a plurality of positions, may also be used for the scattered light receiving unit.

The particle measuring device 100 also includes a processor 8 that receives light reception signals from the scattered light receiving unit 7. In the embodiment illustrated in FIG. 1, the scattered light receiving unit 7 is connected to the processor 8 via a signal transmission unit 9 constituted by a prescribed type of cable. Furthermore, the light reception signals corresponding to the scattered light produced when the particles 4 are irradiated by the resonant laser light 3 are sent to the processor 8 via the signal transmission unit 9 constituted by the cable, and the processor 8 receives those signals. The method used to send and receive the light reception signals is not limited to the cable-based scheme described above. A wireless scheme may also be used. A microcomputer, microprocessor, personal computer, or the like may be used for the processor, and the processor may also function as a power supply unit that supplies electricity to the scattered light receiving unit.

In the embodiment illustrated in FIG. 1, the initial laser light (that is, the laser light before the energy thereof is amplified by the optical resonator 1) is formed by a laser emitter 10 arranged on the side of the reflective mirror 2a of the optical resonator 1 opposite to the side on which the resonant laser light 3 is formed, and this initial laser light enters the optical resonator 1 through the partially transmissive reflective mirror 2a. Next, the basic structure of the laser emitter 10 will be described in more detail. The laser emitter 10 includes a laser medium and a pair of reflective films that face each other and sandwich the laser medium therebetween. Furthermore, due both to the stimulated emission caused when the laser medium receives energy from an excitation source as well as the same mechanism at play in the optical resonator 1, laser light is formed, constituted by energy of a prescribed wavelength that travels back and forth and is stored up between the reflective films. Some of this laser light then exits from a prescribed partially transmissive region formed in one of the reflective films. The laser medium is not particularly limited. Examples of suitable laser mediums include Nd:YVO4 crystals, YAG crystals, or the like.

Moreover, in the embodiment illustrated in FIG. 1, an excitation source generation unit 11 that generates the excitation source for the laser light is connected to the laser emitter 10 via an excitation source transfer unit 12 constituted by an optical fiber cable. The excitation source generated by the excitation source generation unit 11 is coupled into the laser emitter 10 via the excitation source transfer unit 12 constituted by the optical fiber cable. The excitation source generation unit is not particularly limited, and a commercially available pump laser or the like may be used. If the laser medium is an Nd:YVO4 crystal or a YAG crystal, it is preferable that a semiconductor laser in the 800 nm wavelength band be used. The method used to couple in the excitation source is not limited to the optical fiber cable-based scheme described above. A non-contact scheme may also be used.

Furthermore, in the embodiment illustrated in FIG. 1, a reflective mirror adjustment unit 13 that can adjust the angle of the reflective mirror 2b, the distance of the reflective mirror 2b from the reflective mirror 2a, and the like is arranged on the side of the reflective mirror 2b of the optical resonator 1 opposite to the side on which the resonant laser light 3 is formed. A Sigma Koki kinematic mirror holder or the like may be used for the reflective mirror adjustment unit, for example.

In the basic configuration of the particle measuring device of the present invention as described above, the processor outputs light reception pulses according to the light reception signals from the scattered light receiving unit and then calculates the time interval between temporally adjacent light reception pulses. More specifically, the processor includes software and a storage unit such as memory that make it possible to execute processes such as the following, for example: (1) receiving and storing light reception signals from the scattered light receiving unit (2) calculating and storing the intensity of the scattered light according to those signals (3) comparing the calculated scattered light intensity with a pre-stored pulse recognition threshold value or correspondence table to determine which light reception pulses correspond to scattered light from the particles, and outputting those light reception pulses (4) calculating and storing the time intervals between the output light reception pulses that are temporally adjacent. This makes it possible to calculate the time interval between temporally adjacent light reception pulses that correspond to scattered light from the particles.

Figure 3A:
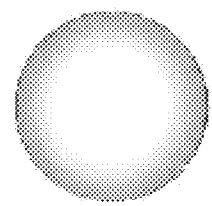
FIGS. 3A to 3F illustrate examples of received scattered light signals corresponding to different laser resonant modes.
Figure 3D:
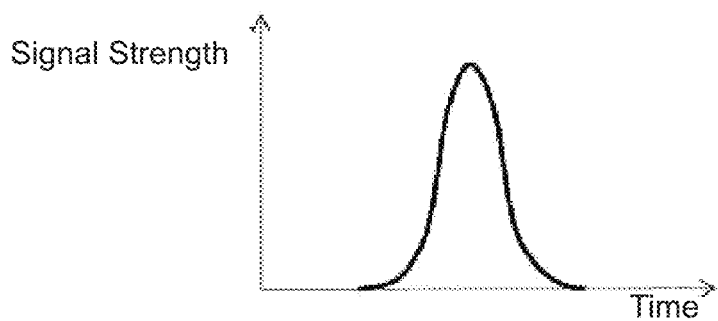
Figure 3B:
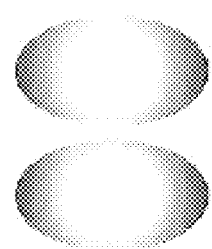
Figure 3E:
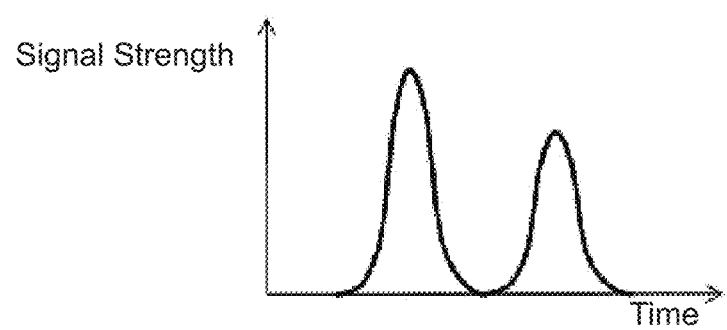
Figure 3C:
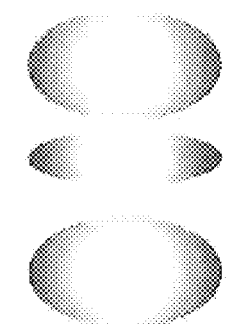
Figure 3F:
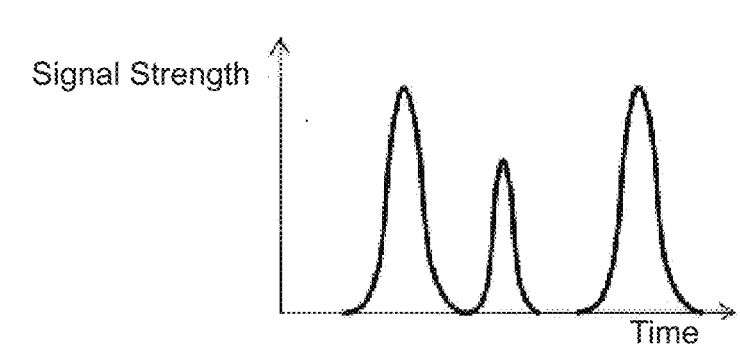

Here, "time interval between temporally adjacent light reception pulses" refers to the time interval between two temporally adjacent light reception pulses corresponding to the scattered light produced when the resonant laser light hits the particles. In most cases, this time interval corresponds to the time interval from after one particle crosses the resonant laser light until the next particle crosses the resonant laser light. However, as described above, typical laser resonant modes include modes such as TEM00, TEM01, and TEM02, and the intensity distributions observed in a cross section of the laser are different for each mode. As illustrated in FIG. 3A, in the TEM00 resonant mode, for example, the laser light intensity distribution is a substantially Gaussian distribution around the center of the beam. As illustrated in FIG. 3D, the intensity of the scattered light from a single particle forms a single pulse on the time axis. However, as illustrated in FIG. 3B, in the TEM01 resonant mode the beam is split into two beams in the vertical direction of the illustrated cross section, and there are two distinct and substantially Gaussian intensity distributions. Therefore, as illustrated in FIG. 3E, when a particle crosses through the illustrated cross section in the vertical direction, two distinct pulses corresponding to the light reception signals from the scattered light thus produced are observed on the time axis. Similarly, as illustrated in FIG. 3C, in the TEM02 resonant mode the beam is split into three beams in the vertical direction of the illustrated cross section, and there are three distinct and substantially Gaussian intensity distributions. Therefore, as illustrated in FIG. 3F, when a particle crosses through the illustrated cross section in the vertical direction, three distinct pulses corresponding to the light reception signals from the scattered light thus produced are observed on the time axis. Therefore, if the resonant mode changes to a mode such as those described above in which more than one pulse is observed when a single particle crosses the laser beam, the phrase "time interval between temporally adjacent light reception pulses" refers to the time interval between those pulses. Consider a case in which the time interval between the single pulses created when particles cross laser light in the TEM00 resonant mode is 10 µs to 100 µs, for example. If the resonant mode changes to a mode in which more than one pulse is observed when a single particle crosses, the new time interval between pulses is normally on the order of 0.1 µs to 100 µs and is sufficiently shorter than the time interval between pulses corresponding to individual particles, thereby making it possible to distinguish between these two types of intervals. More specifically, if a time interval of approximately 1.0 µs to 100 µs between pulses is observed, or even more specifically if a time interval of less than or equal to a prescribed value is observed between pulses, or more realistically if a time interval of approximately 10 µs to 100 µs between pulses is observed, it can be detected that the resonant mode of the resonant laser light has changed.

In order to be able to precisely distinguish between the time intervals between pulses corresponding to individual particles and the time intervals between pulses corresponding to changes in the laser resonant mode according to the differences between the values of those time intervals, it is preferable that the processor 8 include a high speed calculating device (with an operating frequency of greater than or equal to several dozen MHz, for example), a high speed storage device (with an operating frequency of greater than or equal to several dozen MHz, for example), and a high speed voltage comparator (with an operating frequency of greater than or equal to several dozen MHz, for example). Furthermore, using the voltage comparator to detect pulses greater than or equal to a prescribed threshold value in magnitude and using the calculating device to store the detected times in the storage device at a resolution of greater than or equal to 0.1 µs and then calculate the time intervals between pulses makes it possible to precisely distinguish between the time intervals between pulses corresponding to individual particles and the time intervals between pulses corresponding to changes in the laser resonant mode. Moreover, when storing values at a resolution of greater than or equal to 0.1 µs, it is preferable that the speed of the calculating device be at least an order of magnitude greater (several hundred MHz to several GHz, for example) in consideration of the calculating time required.

In a preferred embodiment, the processor outputs the light reception pulses according to the light reception signals received from the scattered light receiving unit, calculates the time interval between temporally adjacent light reception pulses for a plurality of samples, and then calculates a time interval frequency distribution. More specifically, the processor includes software and a storage unit such as memory that make it possible to execute processes such as the following, for example: (1) receiving and storing light reception signals from the scattered light receiving unit (2) calculating and storing the intensity of the scattered light according to those signals (3) comparing the calculated scattered light intensity with a pre-stored pulse recognition threshold value or correspondence table to determine which light reception pulses correspond to scattered light from the particles, and outputting those light reception pulses (4) calculating and storing the time intervals between the output light reception pulses that are temporally adjacent (5) calculating and storing a time interval frequency distribution for a plurality of samples. This makes it possible to calculate the time interval between temporally adjacent light reception pulses that correspond to scattered light from the particles for a plurality of samples, thereby making it possible to calculate a time interval frequency distribution therefor.

Figure 4A:
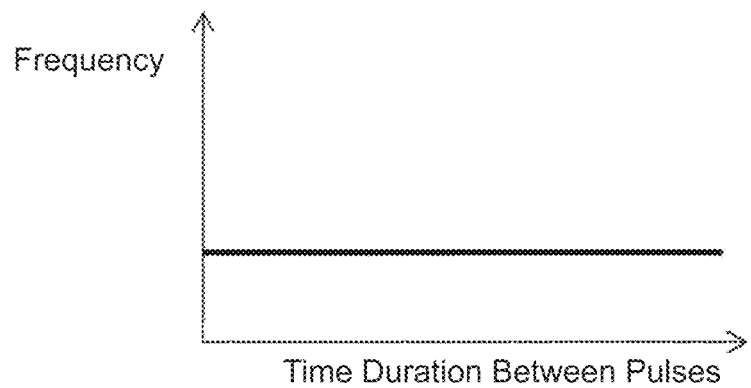
FIGS. 4A to 4C illustrate examples of frequency distributions of the time intervals between pulses for different laser resonant modes.
Figure 4B:
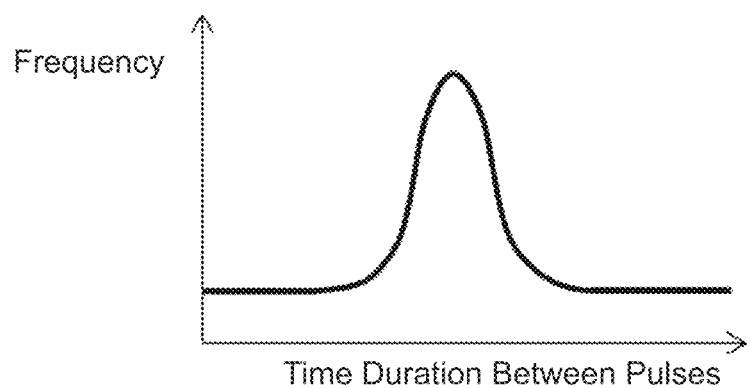
Figure 4C:
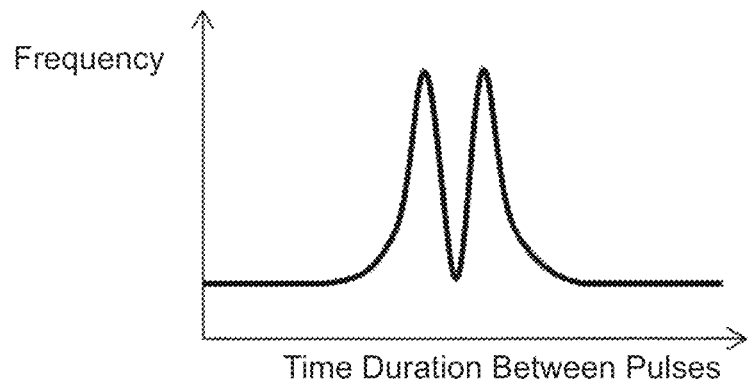

Here, "time interval frequency distribution" refers to a frequency distribution obtained by analyzing the time intervals between two temporally adjacent light reception pulses corresponding to the scattered light produced when the resonant laser light hits the particles for a plurality of samples. In most cases, the particles will cross the laser light at random timings (except under special conditions in which the particles are spaced at fixed intervals, or the like). Therefore, as illustrated in FIG. 4A, in the TEM00 resonant mode (FIGS. 3A and 3D) the frequency distribution of the time intervals between pulses will either not have a peak or will only have a relatively gentle peak. However, as illustrated in FIG. 4B, in the TEM01 resonant mode (FIGS. 3B and 3E), if the speed at which the particles cross the laser light is constant, the frequency distribution of the time intervals between pulses will have a significant peak corresponding to the intensity distribution of the laser light. Similarly, as illustrated in FIG. 4C, in the TEM02 resonant mode (FIGS. 3C and 3F), the frequency distribution will have two significant peaks if the intensity distribution of the laser light is not vertically symmetrical or will have a single significant peak as in FIG. 4B if the intensity distribution of the laser light is vertically symmetrical. As above, consider a case in which the time interval between the single pulses created when particles cross laser light in the TEM00 resonant mode is 10 µs to 100 µs, for example. If the resonant mode changes to a mode in which more than one pulse is observed when a single particle crosses, the new time interval between pulses is normally on the order of 0.1 µs to 100 µs and is sufficiently shorter than the time interval between pulses corresponding to individual particles, thereby making it possible to distinguish between these two types of intervals. More specifically, in the frequency distribution of the time intervals between pulses, if a peak is observed near a time interval of approximately 1.0 µs to 100 µs between pulses, or even more specifically if a peak is observed near a time interval of less than or equal to a prescribed value between pulses, or more realistically if a peak is observed near a time interval of approximately 10 µs to 100 µs between pulses, it can be detected that the resonant mode of the resonant laser light has changed. Using a frequency distribution obtained by analyzing data from a large number of particles as described above with reference to FIGS. 4A to 4C makes it possible to detect the resonant mode of the resonant laser light as well as changes in the resonant mode with higher sensitivity and better precision than when using the pulse data from individual particles as described above with reference to FIGS. 3A to 3F.

As described above, in order to be able to precisely distinguish between the time intervals between pulses corresponding to individual particles and the time intervals between pulses corresponding to changes in the laser resonant mode according to differences in the frequency distribution of the time intervals between pulses, it is preferable that the processor 8 include a high speed calculating device (with an operating frequency of greater than or equal to several dozen MHz, for example), a high speed storage device (with an operating frequency of greater than or equal to several dozen MHz, for example), and a high speed voltage comparator (with an operating frequency of greater than or equal to several dozen MHz, for example). Furthermore, using the voltage comparator to detect pulses greater than or equal to a prescribed threshold value in magnitude and using the calculating device to store the detected times in the storage device at a resolution of greater than or equal to 0.1 µs and then calculate the time intervals between pulses as well as the frequency distribution thereof makes it possible to precisely distinguish between the time intervals between pulses corresponding to individual particles and the time intervals between pulses corresponding to changes in the laser resonant mode. Moreover, when storing values at a resolution of greater than or equal to 0.1 µs, it is preferable that the speed of the calculating device be at least an order of magnitude greater (several hundred MHz to several GHz, for example) in consideration of the calculating time required.

In a preferred embodiment, the processor determines the resonant mode of the resonant laser light according to the time intervals between pulses and/or according to a frequency distribution of the time intervals between pulses for a plurality of samples, as described above. More specifically, the processor includes software and a storage unit such as memory that make it possible to execute processes such as the following, for example: (1) receiving and storing light reception signals from the scattered light receiving unit (2) calculating and storing the intensity of the scattered light according to those signals (3) comparing the calculated scattered light intensity with a pre-stored pulse recognition threshold value or correspondence table to determine which light reception pulses correspond to scattered light from the particles, and outputting those light reception pulses (4) calculating and storing the time intervals between the output light reception pulses that are temporally adjacent (5) calculating and storing a time interval frequency distribution for a plurality of samples (6) comparing the calculated time intervals between pulses and/or the frequency distribution thereof to a pre-stored threshold value or correspondence table for determining changes in the resonant mode, and determining whether the resonant mode has changed or to what extent the resonant mode has changed. This makes it possible to determine the resonant mode of the resonant laser light. In this case, the processor may be a personal computer, for example, and notifications may be displayed to the user according to the results of the determination.

Figure 5:
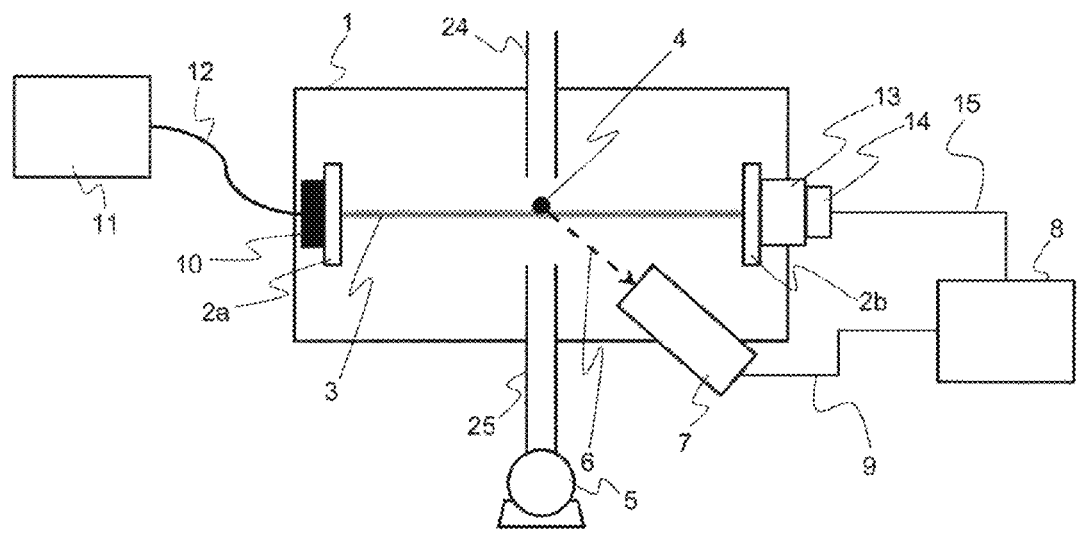
FIG. 5 is a plan view schematically illustrating a particle measuring device according to Embodiment 2 of the present invention.

FIG. 5 schematically illustrates the configuration of a particle measuring device 200 according to Embodiment 2 of the present invention. The particle measuring device 200 is the same as the particle measuring device 100 described above but also includes an actuator 14 that can convert electrical signals to mechanical displacements for the reflective mirror adjustment unit 13, and adjustment signals from the processor 8 are sent to the actuator 14 via a signal transmission unit 15 constituted by a prescribed type of cable. Furthermore, the actuator 14 can be controlled according to the abovementioned determination of whether the resonant mode has changed or to what extent the resonant mode has changed, or the like. More specifically, the processor includes software and a storage unit such as memory that make it possible to execute processes such as the following, for example: (1) receiving and storing light reception signals from the scattered light receiving unit (2) calculating and storing the intensity of the scattered light according to those signals (3) comparing the calculated scattered light intensity with a pre-stored pulse recognition threshold value or correspondence table to determine which light reception pulses correspond to scattered light from the particles, and outputting those light reception pulses (4) calculating and storing the time intervals between the output light reception pulses that are temporally adjacent (5) calculating and storing a time interval frequency distribution for a plurality of samples (6) comparing the calculated time intervals between pulses and/or the frequency distribution thereof to a pre-stored threshold value or correspondence table for determining changes in the resonant mode, and determining whether the resonant mode has changed or to what extent the resonant mode has changed (7) comparing the results of the determination to a pre-stored threshold value or correspondence table for generating commands for the actuator, and sending adjustment signals to the actuator. This makes it possible to control the operation of the actuator 14. This embodiment makes it possible to automatically control the laser resonant mode using feedback control, thereby making it possible to guarantee long-term precision of measurements without the need for the user to do anything.

It will be apparent to those skilled in the art that various modifications and variations can be made in the present invention without departing from the spirit or scope of the invention. Thus, it is intended that the present invention cover modifications and variations that come within the scope of the appended claims and their equivalents. In particular, it is explicitly contemplated that any part or whole of any two or more of the embodiments and their modifications described above can be combined and regarded within the scope of the present invention.

What is claimed is:

1. A particle measuring device for measuring particles in an aerosol, comprising:
    an optical resonator that causes laser light to travel back and forth between two opposing reflective mirrors in order to amplify an energy of the laser light and form resonant laser light;
    a particle transport unit configured to transport the particles in the aerosol across a beam path of the resonant laser light so as to generate a stream of the particles crossing the beam path;
    a scattered light receiving unit configured to receive scattered light that is produced when the particles in the aerosol are irradiated by the resonant laser light, and output a light reception signal in accordance with the received scattered light for each scattering event; and
    a processor that receives the light reception signal from the scattered light receiving unit for each event of the reception of the scattered light,
    wherein the processor outputs a light reception pulse in accordance with each light reception signal from the scattered light receiving unit, and derives time intervals between light reception pulses that are temporally adjacent, and
    wherein the processor compares the derived time interval with a prescribed threshold time interval, and, if the derived time interval is less than or equal to the prescribed threshold time interval, the processor determines that the corresponding two adjacent light reception pulses are caused by a single particle crossing the beam path, and if the derived time interval is greater than the prescribed threshold time interval, the processor determines that the corresponding two adjacent light reception pulses are caused by two particles crossing the beam path successively.

2. The particle measuring device according to claim 1, wherein the processor further derives a frequency distribution of the derived time intervals, and sets said prescribed threshold time interval in accordance with the frequency distribution.

3. The particle measuring device according to claim 1, wherein the processor determines a resonant mode of the resonant laser light based on one or more of the derived time intervals between the adjacent pulses or a frequency distribution of the derived time intervals, and sets said prescribed threshold tine interval in accordance with the determined mode of the resonance laser light.

4. The particle measuring device according to claim 3, wherein the optical resonator includes a reflective mirror adjustment unit that adjusts the reflective mirrors in accordance with the determination of the resonant mode by the processor.

5. The particle measuring device according to claim 1, wherein the particles in the aerosol cross the beam path of the resonant laser light formed by the optical resonator inside the optical resonator.

6. The particle measuring device according to claim 1, wherein in the optical resonator, a laser emitter is provided on a surface of one of the reflective mirrors on a side thereof opposite to where the resonant laser light is formed, and the optical resonator is configured such that laser light produced by introducing a prescribed excitation source to the laser emitter enters the optical resonator through said one of the reflective mirrors and goes on to become the resonant laser light.

7. A particle measuring device for measuring particles in an aerosol, comprising:
    an optical resonator that causes laser light to travel back and forth between two opposing reflective mirrors in order to amplify an energy of the laser light and form resonant laser light;
    a particle transport unit configured to transport the particles in the aerosol across a beam path of the resonant laser light so as to generate a stream of the particles crossing the beam path;
    a scattered light receiving unit configured to receive scattered light that is produced when the particles in the aerosol are irradiated by the resonant laser light, and output a light reception signal in accordance with the received scattered light for each scattering event; and
    a processor that receives the light reception signal from the scattered light receiving unit for each event of the reception of the scattered light,
    wherein the processor outputs a light reception pulse in accordance with each light reception signal from the scattered light receiving unit, and derives time intervals between light reception pulses that are temporally adjacent,
    wherein the processor derives a frequency distribution of the derived time intervals, and determines the number of the light reception pulses that are generated as a result of a single particle crossing the beam path, which depends on a resonant mode of the resonant laser light, based on the derived frequency distribution of the derived time intervals, and
    wherein the processor counts the number of the particles crossing the beam path in accordance with the determined number of light reception pulses that are generated as a result of a single particle crossing the beam path.

8. The particle measuring device according to claim 7, wherein the processor determines the resonant mode of the resonant laser light based on the frequency distribution of the derived time intervals.

9. The particle measuring device according to claim 8, wherein the optical resonator includes a reflective mirror adjustment unit that adjusts the reflective mirrors in accordance with the determination of the resonant mode by the processor.

10. The particle measuring device according to claim 7, wherein the particles in the aerosol cross the beam path of the resonant laser light formed by the optical resonator inside the optical resonator.

11. The particle measuring device according to claim 7, wherein in the optical resonator, a laser emitter is provided on a surface of one of the reflective mirrors on a side thereof opposite to where the resonant laser light is formed, and the optical resonator is configured such that laser light produced by introducing a prescribed excitation source to the laser emitter enters the optical resonator through said one of the reflective mirrors and goes on to become the resonant laser light.

\* \* \* \* \*